US00PP27700P3

(12) United States Plant Patent
Kirsten

(10) Patent No.: US PP27,700 P3
(45) Date of Patent: Feb. 21, 2017

(54) ***AGAPANTHUS* PLANT NAMED 'KEK 5006'**

(50) Latin Name: *Agapanthus praecox*
Varietal Denomination: KEK 5006

(71) Applicant: Keith Kirsten, Lindley (ZA)

(72) Inventor: Keith Kirsten, Lindley (ZA)

( * ) Notice: Subject to any disclaimer, the term of this patent is extended or adjusted under 35 U.S.C. 154(b) by 64 days.

(21) Appl. No.: 14/545,614

(22) Filed: May 28, 2015

(65) Prior Publication Data

US 2016/0353646 P1 Dec. 1, 2016

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Anne Grunberg
(74) *Attorney, Agent, or Firm* — Cassandra Bright

(57) ABSTRACT

A new and distinct *Agapanthus* cultivar named 'KEK 5006' is disclosed, characterized by, green foliage with a distinct yellow margin. Plants are consistently variegated and easier to propagate than most variegated *Agapanthus*. The new variety is a *Agapanthus*, typically produced as an outdoor ornamental plant.

2 Drawing Sheets

Figure 1:
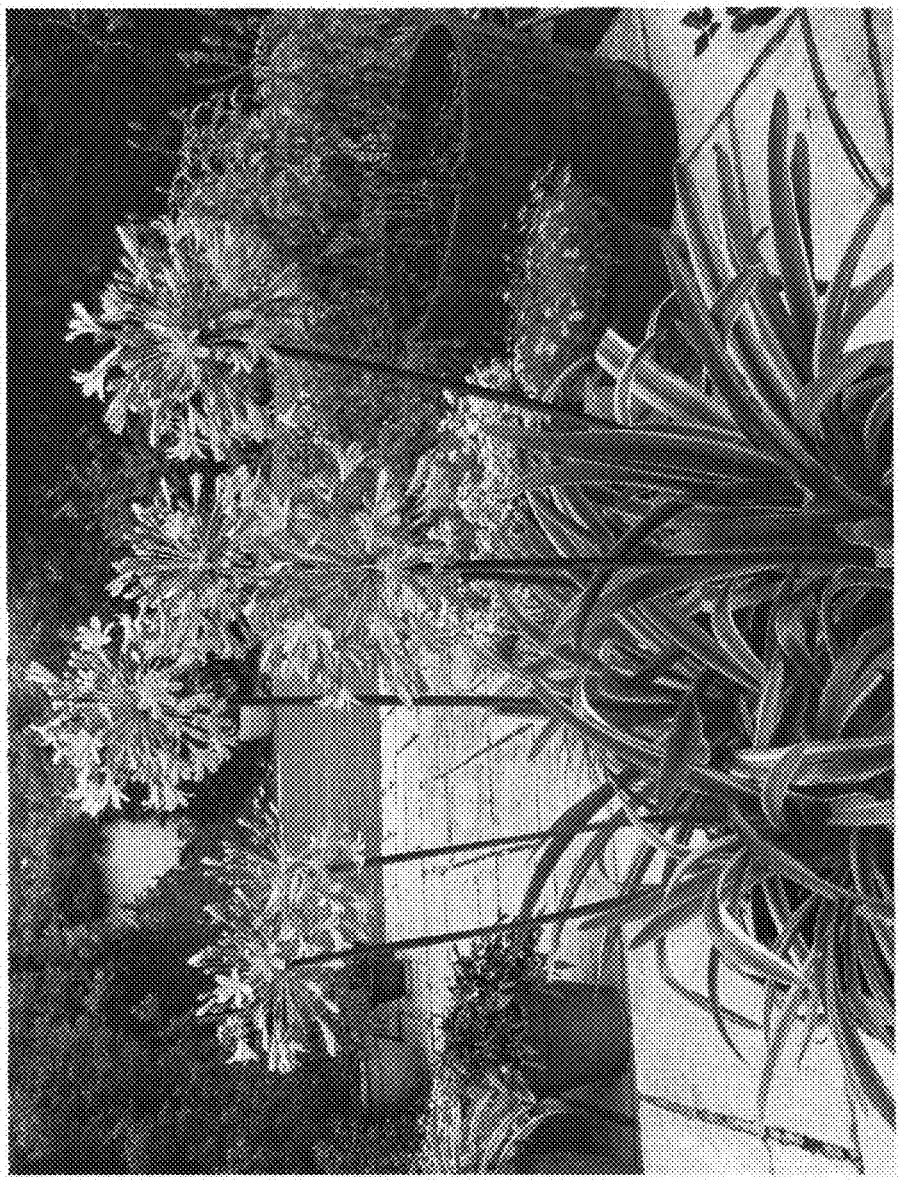

Latin name of the genus and species: *Agapanthus praecox*.

Variety denomination: 'KEK 5006'.

BACKGROUND OF THE INVENTION

The new cultivar is the product of chance discovery. The new variety originated as a naturally occurring, whole plant mutation of an unpatented, unnamed *Agapanthus praecox*.

The new variety was discovered by the inventor after several years of isolating and propagating clones of the interesting *Agapanthus praecox* mutation in a commercial nursery in Lanseria, South Africa. After identifying the new variety as a potentially interesting selection, the inventor continued confidential testing and observation of 'KEK 5006' until approximately 1997, finally selecting the variety 'KEK5006' for further propagation during 2000.

Asexual reproduction of the new cultivar 'KEK 5006' was first performed by division in Lanseria, South Africa, during 2000, on a very limited basis. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'KEK 5006' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KEK 5006'. These characteristics in combination distinguish 'KEK 5006' as a new and distinct *Agapanthus* cultivar:

1. Broad, variegated foliage.
2. Very stable variegation, without reversion.

3. Faster growing than typical variegated *Agapanthus*.
4. Green foliage with a bright yellow margin.

PARENT COMPARISON

Plants of the new cultivar 'KEK 5006' are similar to the parent in most horticultural characteristics. However, the new variety, produces very stable variegated foliage, compared to the parent plant, which reverts more easily. Additionally, plants of 'KEK 5006' produce flowers of a lighter blue than the parent variety.

COMMERCIAL COMPARISON

Plants of the new cultivar 'KEK 5006' are similar to the unpatented commercial variety *Agapanthus praecox* 'Tinkerbell' in most horticultural characteristics. The new variety, however, differs in the following:

1. Produces foliage that is green with yellow variegation, whereas 'Tinkerbell' produces silver-green variegated leaves.
2. 'KEK 5006' consistently produces flowers regularly whereas 'Tinkerbell' flowers infrequently and erratically. Foliage of the new variety is broader than foliage of 'Tinkerbell'.
3. Broader foliage than 'Tinkerbell'.
4. Flowers of the new variety produce a lighter color blue than flowers of 'Tinkerbell'.
5. Plants of the new variety are on average 20 cm taller.

Plants of the new cultivar 'KEK 5006' are similar to the commercial variety *Agapanthus africanus* 'Summer Gold', unpatented, in most horticultural characteristics. The new variety, however, differs in the following:

1. Plants of the new variety are taller than plants of 'Summer Gold'.
2. Flowers of the new variety produce a much lighter color blue than flowers of 'Summer Gold'.
3. Plants of the new variety have a lighter yellow variegation 4. Plants of the new variety are easier to propagate than plants of 'Summer Gold'.
5. Foliage of the new variety is much broader than foliage of 'Summer Gold'.

BRIEF DESCRIPTION OF THE PHOTOGRAPHS

The accompanying photograph in FIG. 1 illustrates in full color a typical plant of 'KEK 5006' grown in Lanseria, South Africa.

Figure 2:
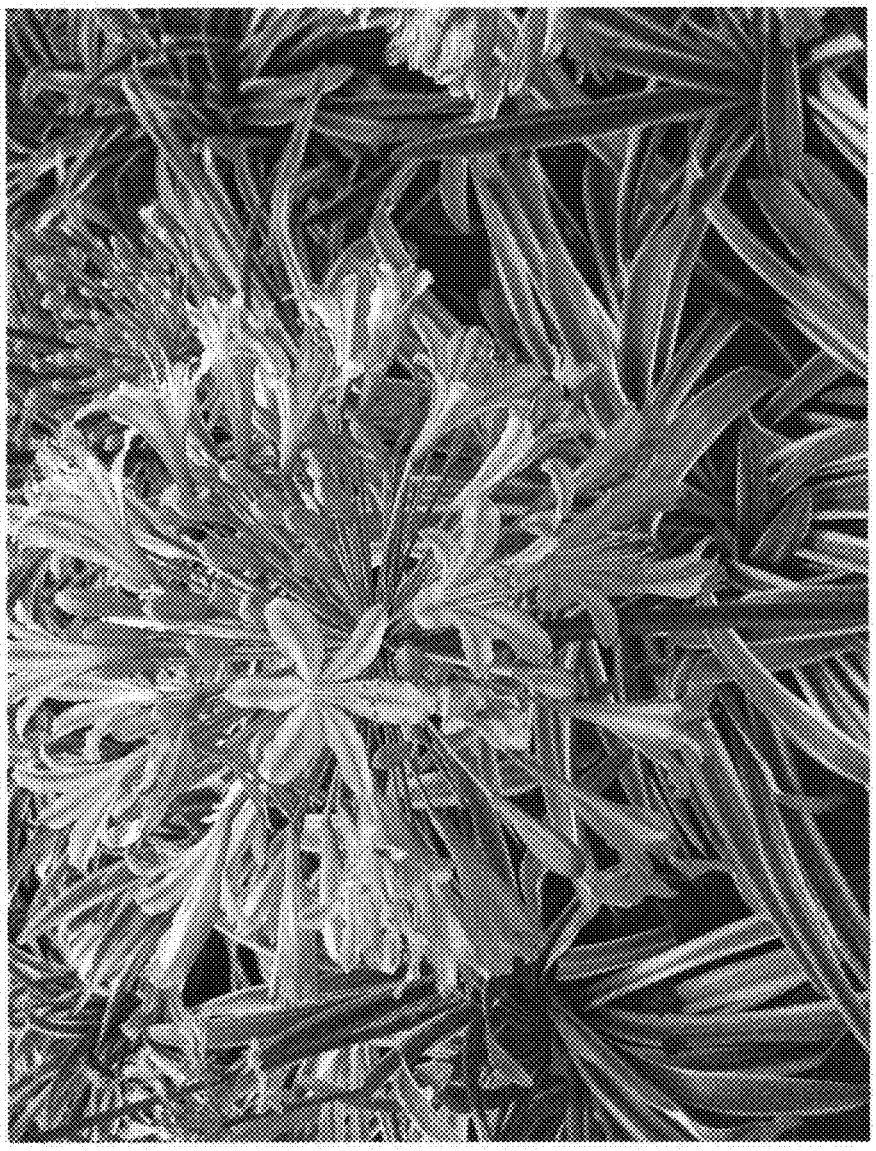

FIG. 2 illustrates in full color a close up of the inflorescence and foliage of 'KEK 5006'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KEK 5006' plants grown outdoors in San Juan Capistrano, Calif. Plants are approximately 1 year old. Temperatures ranged from approximately 8° C. to 25° C. at night and 10° C. to 32° C. during the day. No artificial light, photoperiodic treatments were given to the plants. No chemical treatments were given to plants. Measurements and numerical values represent averages of typical plant types.

Botanical classification: *Agapanthus praecox* 'KEK 5006'.

PROPAGATION

Root description: Thick, fleshy root system colored near Greyed-Orange 164D and Orange-White 159C.

PLANT

Growth habit: Clump forming tender perennial with arching, pendulous foliage.

Height: Foliar plane 30 to 40 cm. Flowering plane up to 75 cm.

Plant spread: Approximately 75 cm.

Growth rate: Moderate, slower growth than non-variegated forms.

Growth pattern: The plant grows throughout most of the year but mainly in the summer months. This grow is in the form of basal shoots or pups as well as some leaf extension. From mid summer flowers start to appear and remain for much of the summer.

FOLIAGE

Leaf:

*Average leaf length*.—Average range approximately 25 to 40 cm.

*Average leaf width*.—Approximately 3.5 cm.

*Arrangement*.—Basal, irregular whorls.

*Shape of blade*.—Linear.

*Apex*.—Acute.

*Base*.—Cuneate.

*Margin*.—Entire.

*Texture of top surface*.—Smooth.

*Texture of bottom surface*.—Smooth.

*Quantity of leaves per plant*.—Average 25.

*Color*.—Leaf color is influenced by the amount of sun exposure. Information below relates to plants under shade cloth. Both mature and immature foliage colored the same. Upper blade: Margin near Yellow 11D, margin width average 7 mm. Interior colored near Green 138A, with thin(about 2 to 3 mm) stripes colored near Yellow 11D. Lower Blade: Near Green group RHS Yellow-Green 144A.

*Venation*.—Type: Linear. Venation color upper side: Indistinguishable from leaf blade. Venation color under side: Indistinguishable from leaf blade.

FLOWER

Natural flowering season: Summer.

Length of flowering period: Approximately 8 weeks.

Inflorescence type: Terminal Umbel with approximately 44 individual flowers.

Individual flower type: Single.

Flower profile: Funnelform.

Bud:

*Shape*.—Ovate.

*Shape*.—Narrow ovate.

*Length*.—Approximately 3.1 cm.

*Diameter*.—Approximately 0.9 cm.

*Color*.—Near Violet-Blue 95D, striped with 94C.

Umbel size:

*Diameter*.—Average 16 cm.

*Height*.—Average 11 cm.

*Stem length*.—Average 50 to 60 cm.

Corolla:

*Arrangement*.—Apetalous, single, campanulate flowers composed of 6 basally fused tepals, shaped into a flared trumpet.

*Size*.—Length: Approximately 4.1 cm. Width: Approximately 3.6 cm at widest point. Lobe Length: Approximately 2.1 cm. Lobe Width: 0.4 cm.

*Margin*.—Entire.

*Shape*.—Lanceolate.

*Apex*.—Obtuse, concave.

*Texture*.—Glabrous all surfaces.

Color:

*Tepals*.—When opening: Outer surface: Near Violet-Blue 95D striped 94D. Inner surface: A color between Violet-Blue 94D and 95D. Center stripe near Violet-Blue 97A.

*Fully opened*.—Outer surface: Near RHS Violet-Blue 97D with center streak near 94D. Inner surface: Near RHS Violet-Blue 97C with center streak near 97A.

*Color changes when aging*.—Outer surface: Near RHS Violet-Blue 97D with center streak near Violet N87D. Inner surface: Near RHS Violet-Blue 91C with center streak near Violet N87D.

*Sepals*.—Not Present.

Fragrance: None.

Pedicels:

*Length*.—Approximately 2.9 cm.

*Width*.—Approximately 0.15 cm.

*Aspect*.—Straight.

*Color*.—Near RHS Yellow-Green 144A, striped Green 138B.

Scape:

*Length*.—Average range 50 to 60 cm.

*Width*.—Approximately 0.9 cm.

*Angle*.—Upright from center of plant, very straight.
*Strength*.—Strong.
*Color*.—Near RHS Green 138B, striped Yellow 9D.
Flower filament color: Near Violet-Blue group RHS 94C.
Flower anther color: Near Greyed-Yellow group RHS 160D
Flower style color: Near Violet-Blue group RHS 94C.

REPRODUCTIVE ORGANS

Stamens:
*Number*.—Average 6.
*Filament length*.—Approximately 2.8 cm.
*Filament color*.—Near RHS Violet-Blue 91D.
*Anther length*.—0.2 cm.
*Anther color*.—Near RHS Purple N79C.
*Pollen*.—Not observed.
Pistil:
*Number*.—1.
*Length*.—Approximately 2.6 cm.
*Style color*.—Near RHS Violet-Blue 92D.
*Stigma*.—Shape: Linear. Color: Near RHS Violet-Blue 91D.
*Ovary color*.—Near RHS Yellow-Green 150B.

OTHER CHARACTERISTICS

Seed production: Seed production not observed to date.
Disease resistance: Neither resistance nor susceptibility to normal diseases and pests of *Agapanthus*.
Temperature tolerance: Typically USDA zones 7*b* through 11.
Drought tolerance: Will tolerate considerable dryness once established.

What is claimed is:

1. A new and distinct cultivar of *Agapanthus* plant named 'KEK 5006' as herein illustrated and described.

* * * * *